US008288358B2

(12) United States Patent
Foster et al.

(10) Patent No.: US 8,288,358 B2
(45) Date of Patent: Oct. 16, 2012

(54) THERAPEUTIC TARGETS AND MOLECULES

(75) Inventors: Paul Stephen Foster, Merewether (AU); Joerg Mattes, Merewether (AU)

(73) Assignee: Newcastle Innovation Ltd., Callaghan (AU)

(*) Notice: Subject to any disclaimer, the term of this patent is extended or adjusted under 35 U.S.C. 154(b) by 19 days.

(21) Appl. No.: 12/593,066

(22) PCT Filed: Mar. 26, 2008

(86) PCT No.: PCT/AU2008/000430
§ 371 (c)(1),
(2), (4) Date: Dec. 30, 2009

(87) PCT Pub. No.: WO2008/116267
PCT Pub. Date: Oct. 2, 2008

(65) Prior Publication Data
US 2010/0113562 A1   May 6, 2010

Related U.S. Application Data

(60) Provisional application No. 60/907,208, filed on Mar. 26, 2007.

(30) Foreign Application Priority Data

Mar. 26, 2007 (AU) .............................. 2007901595

(51) Int. Cl.
C12N 15/11 (2006.01)
C07H 21/04 (2006.01)
(52) U.S. Cl. ..................................... 514/44 A; 536/24.5
(58) Field of Classification Search ........................ None
See application file for complete search history.

(56) References Cited

FOREIGN PATENT DOCUMENTS

| WO | WO 2004/076622 A2 | 9/2004 |
| WO | WO 2006/027776 A2 | 3/2006 |
| WO | WO 2006/097768 A2 | 9/2006 |
| WO | WO 2006/011512 | 10/2006 |
| WO | WO 2006/128245 A1 | 12/2006 |
| WO | WO 2006/137941 | 12/2006 |
| WO | WO 2007/087539 A2 | 8/2007 |
| WO | WO 2007/112754 A2 | 10/2007 |

OTHER PUBLICATIONS

Mahajan (Continuing Education in Anaesthesia, Critical Care & Pain, 5(2): 52-55, 2005).*
Bel (Current Opinion in Pulmonary Medicine 2004, 10:44-50).*
Taylor (J. Allergy Clin. Immunol. (Feb. 2006) vol. 117, No. 2, pp. 259-262).*
Mattes et al (PNAS 106(44): 18704-18709, 2009).*
Collison et al (BMC Pulmonary Medicine 2011, 11:29, 6 pages).*
Supplementary European Search Report for European Patent Application No. 08 71 4472 dated Mar. 3, 2011.
Yang, Employment of MicroRNA Profiles and RNA Interference and Antagomirs for the Characterization and Treatment of Respiratory Disease, Drug Discovery Today: Therapeutic Strategies, Nov. 23, 2006, vol. 3, No. 3, pp. 325-332.
Tan et al., A Polymorphism in the HLA-G 3-UTR Influences Targeting of MIR-148 and is Associated with Asthma, Feb. 2006, vol. 117, No. 2, p. S141 (Abstract only).
Yanaihara et al., Unique MicroRNA Molecular Profiles in Lung Cancer Diagnosis and Prognosis, Cancer Cell, Mar. 1, 2006, vol. 9, No. 3, pp. 189-198.
Krutzfeldt et al., Silencing of MicroRNA's in Vivo with Antagomirs, Nature Publishing Group, Dec. 2005, vol. 438, No. 7068, pp. 685-689.
Lagos et al., Identification of Tissue-Specific MicroRNAs from Mouse, Current Biology, Apr. 30, 2002, vol. 12, No. 9, pp. 735-739.
Popescu et al., A Review of Antisense Therapeutic Interventions for Molecular Biological Targets in Asthma, Biologics: Targets & Therapy, Jan. 21, 2007, pp. 271-283.
Mattes et al., Regulation of MicroRNA by Antagomirs, American Journal of Respiratory Cell and Molecular Biology, vol. 36, No. 1, pp. 8-12, 200 Jun. 8, 2012.
O'Connell Ryan et al.: MicroRNA-155 is induced during the macrophage inflammatory response: PNAS, vol. 104, No. 5, Jan. 30, 2007, pp. 1604-1609.
Taganov Konstantin D. et al.: NF-κB-dependent induction of microRNA miR-146, an inhibitor targeted to signaling proteins of innate immune responses: PNAS, vol. 103, No. 33, Aug. 15, 2006, pp. 12481-12486.
Weiler J et al.: Anti-mRNA oligonucleotides (AMOs): ammunition to target miRNAs implicated in human disease: Gene Therapy, vol. 13 No. 6, 2006, pp. 496-502.

* cited by examiner

Primary Examiner — Richard Schnizer
(74) Attorney, Agent, or Firm — Roylance, Abrams, Berdo & Goodman, L.L.P.

(57) ABSTRACT

The invention provides methods and compositions for treating or preventing inflammation or an inflammatory condition in a subject, comprising administering to the subject an effective amount of at least one antagonist of one or more miRNA upregulated in inflammatory disease conditions and response to allergen challenge. The invention also provides methods for diagnosing inflammatory conditions based on miRNA expression profile signatures.

5 Claims, 4 Drawing Sheets

```
                        SEQUENCE LISTING

<160> NUMBER OF SEQ ID NOS: 63

<210> SEQ ID NO 1
<211> LENGTH: 22
<212> TYPE: RNA
<213> ORGANISM: Homo sapiens

<400> SEQUENCE: 1
uagcuuauca gacugauguu ga                                            22

<210> SEQ ID NO 2
<211> LENGTH: 24
<212> TYPE: RNA
<213> ORGANISM: Homo sapiens

<400> SEQUENCE: 2
guccaguuuu cccaggaauc ccuu                                          24

<210> SEQ ID NO 3
<211> LENGTH: 22
<212> TYPE: RNA
<213> ORGANISM: Homo sapiens

<400> SEQUENCE: 3 uuggucccu ucaaccagcu gu                                             22

<210> SEQ ID NO 4
<211> LENGTH: 22
```

```
<212> TYPE: RNA
<213> ORGANISM: Homo sapiens

<400> SEQUENCE: 4
uguaaacauc cucgacugga ag                                          22

<210> SEQ ID NO 5
<211> LENGTH: 21
<212> TYPE: RNA
<213> ORGANISM: Homo sapiens

<400> SEQUENCE: 5
uagcaccauc ugaaaucggu u                                           21

<210> SEQ ID NO 6
<211> LENGTH: 22
<212> TYPE: RNA
<213> ORGANISM: Homo sapiens

<400> SEQUENCE: 6
aagcugccag uugaagaacu gu                                          22

<210> SEQ ID NO 7
<211> LENGTH: 21
<212> TYPE: RNA
<213> ORGANISM: Homo sapiens

<400> SEQUENCE: 7
uucacagugg cuaaguuccg c                                           21

<210> SEQ ID NO 8
<211> LENGTH: 21
<212> TYPE: RNA
<213> ORGANISM: Homo sapiens

<400> SEQUENCE: 8
aucacauugc cagggauuac c                                           21

<210> SEQ ID NO 9
<211> LENGTH: 21
<212> TYPE: RNA
<213> ORGANISM: Homo sapiens

<400> SEQUENCE: 9
aucacauugc cagggauuuc c                                           21

<210> SEQ ID NO 10
<211> LENGTH: 22
<212> TYPE: RNA
<213> ORGANISM: Homo sapiens

<400> SEQUENCE: 10
ugagguagua gguuguauag uu                                          22

<210> SEQ ID NO 11
<211> LENGTH: 22
<212> TYPE: RNA
<213> ORGANISM: Homo sapiens

<400> SEQUENCE: 11
ugagguagua gguugugugg uu                                          22

<210> SEQ ID NO 12
<211> LENGTH: 22
```

<212> TYPE: RNA
<213> ORGANISM: Homo sapiens

<400> SEQUENCE: 12
ugagguagua gguuguaugg uu                                              22

<210> SEQ ID NO 13
<211> LENGTH: 22
<212> TYPE: RNA
<213> ORGANISM: Homo sapiens

<400> SEQUENCE: 13
uagcagcacg uaaauauugg cg                                              22

<210> SEQ ID NO 14
<211> LENGTH: 21
<212> TYPE: RNA
<213> ORGANISM: Homo sapiens

<400> SEQUENCE: 14
ucguaccgug aguaauaaug c                                               21

<210> SEQ ID NO 15
<211> LENGTH: 21
<212> TYPE: RNA
<213> ORGANISM: Homo sapiens

<400> SEQUENCE: 15
ugucaguuug ucaaauaccc c                                               21

<210> SEQ ID NO 16
<211> LENGTH: 23
<212> TYPE: RNA
<213> ORGANISM: Homo sapiens

<400> SEQUENCE: 16
gugccuacug agcugauauc agu                                             23

<210> SEQ ID NO 17
<211> LENGTH: 23
<212> TYPE: RNA
<213> ORGANISM: Homo sapiens

<400> SEQUENCE: 17
uguaaacauc cuacacucuc agc                                             23

<210> SEQ ID NO 18
<211> LENGTH: 22
<212> TYPE: RNA
<213> ORGANISM: Homo sapiens

<400> SEQUENCE: 18
cauugcacuu gucucggucu ga                                              22

<210> SEQ ID NO 19
<211> LENGTH: 22
<212> TYPE: RNA
<213> ORGANISM: Homo sapiens

<400> SEQUENCE: 19
uagcagcaca ucaugguuua ca                                              22

<210> SEQ ID NO 20
<211> LENGTH: 22

```
<212> TYPE: RNA
<213> ORGANISM: Homo sapiens

<400> SEQUENCE: 20
aacauucauu gcugucggug gg                                          22

<210> SEQ ID NO 21
<211> LENGTH: 22
<212> TYPE: RNA
<213> ORGANISM: Homo sapiens

<400> SEQUENCE: 21
ucucccaacc cuuguaccag ug                                          22

<210> SEQ ID NO 22
<211> LENGTH: 22
<212> TYPE: RNA
<213> ORGANISM: Homo sapiens

<400> SEQUENCE: 22
uuaucagaau cuccaggggu ac                                          22

<210> SEQ ID NO 23
<211> LENGTH: 21
<212> TYPE: RNA
<213> ORGANISM: Homo sapiens

<400> SEQUENCE: 23
ugcugacucc uaguccaggg c                                           21

<210> SEQ ID NO 24
<211> LENGTH: 23
<212> TYPE: RNA
<213> ORGANISM: Homo sapiens

<400> SEQUENCE: 24
acuccauuug uuuugaugau gga                                         23

<210> SEQ ID NO 25
<211> LENGTH: 23
<212> TYPE: RNA
<213> ORGANISM: Homo sapiens

<400> SEQUENCE: 25
aacauucaac gcugucggug agu                                         23

<210> SEQ ID NO 26
<211> LENGTH: 22
<212> TYPE: RNA
<213> ORGANISM: Mus musculus

<400> SEQUENCE: 26
aaagugcuuc ccuuuugugu gu                                          22

<210> SEQ ID NO 27
<211> LENGTH: 23
<212> TYPE: RNA
<213> ORGANISM: Mus musculus

<400> SEQUENCE: 27
ccuaguaggu gcucaguaag ugu                                         23

<210> SEQ ID NO 28
<211> LENGTH: 22
```

-continued

```
<212> TYPE: RNA
<213> ORGANISM: Artificial Sequence
<220> FEATURE:
<223> OTHER INFORMATION: Synthetic oligonucleotide

<400> SEQUENCE: 28
ucaacaucag ucugauaagc ua                                                  22

<210> SEQ ID NO 29
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 29
aagggauucc ugggaaaacu ggac                                                24

<210> SEQ ID NO 30
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 30
acagcugguu gaaggggacc aa                                                  22

<210> SEQ ID NO 31
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 31
cuuccagucg aggauguuua ca                                                  22

<210> SEQ ID NO 32
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 32
aaccgauuuc agauggugcu a                                                   21

<210> SEQ ID NO 33
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 33
acaguucuuc aacuggcagc uu                                                  22

<210> SEQ ID NO 34
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 34
gcggaacuua gccacuguga a                                                   21
```

```
<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 35
gguaaucccu ggcaauguga u                                           21

<210> SEQ ID NO 36
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 36
ggaaaucccu ggcaauguga u                                           21

<210> SEQ ID NO 37
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 37
aacuauacaa ccuacuaccu ca                                          22

<210> SEQ ID NO 38
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 38
aaccacacaa ccuacuaccu ca                                          22

<210> SEQ ID NO 39
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 39
aaccauacaa ccuacuaccu ca                                          22

<210> SEQ ID NO 40
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 40
cgccaauauu uacgugcugc ua                                          22

<210> SEQ ID NO 41
<211> LENGTH: 21
<212> TYPE: RNA
<213> ORGANISM: Artificial Sequence
<220> FEATURE:
<223> OTHER INFORMATION: Synthetic oligonucleotide
```

-continued

<400> SEQUENCE: 41
gcauuauuac ucacgguacg a                                              21

<210> SEQ ID NO 42
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 42
gggguauuug acaaacugac a                                              21

<210> SEQ ID NO 43
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 43
acugauauca gcucaguagg cac                                            23

<210> SEQ ID NO 44
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 44
gcugagagug uaggauguuu aca                                            23

<210> SEQ ID NO 45
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 45
ucagaccgag acaagugcaa ug                                             22

<210> SEQ ID NO 46
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 46
uguaaaccau gaugugcugc ua                                             22

<210> SEQ ID NO 47
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 47
cccaccgaca gcaaugaaug uu                                             22

<210> SEQ ID NO 48
<211> LENGTH: 22

-continued

<212> TYPE: RNA
<213> ORGANISM: Artificial Sequence
<220> FEATURE:
<223> OTHER INFORMATION: Synthetic oligonucleotide

<400> SEQUENCE: 48
cacugguaca agguuuggga ga                                              22

<210> SEQ ID NO 49
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 49
guaccccugg agauucugau aa                                              22

<210> SEQ ID NO 50
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 50
gcccuggacu aggagucagc a                                               21

<210> SEQ ID NO 51
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 51
uccaucauca aaacaaaugg agu                                             23

<210> SEQ ID NO 52
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 52
acucaccgac agcguugaau guu                                             23

<210> SEQ ID NO 53
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 53
acacacaaaa gggaagcacu uu                                              22

<210> SEQ ID NO 54
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 54
acacuuacug agcaccuacu agg                                             23

```
<210> SEQ ID NO 55
<211> LENGTH: 22
<212> TYPE: RNA
<213> ORGANISM: Homo sapiens

<400> SEQUENCE: 55
ugagguagua gauuguauag uu                                              22

<210> SEQ ID NO 56
<211> LENGTH: 21
<212> TYPE: RNA
<213> ORGANISM: Artificial Sequence
<220> FEATURE:
<223> OTHER INFORMATION: Sytnthetic oligonucleotide
<220> FEATURE:
<221> NAME/KEY: modified_base
<222> LOCATION: (1)..(21)
<223> OTHER INFORMATION: 2'-OMe modified phosphoramidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (18)..(19)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage

<400> SEQUENCE: 56
gcauuauuac ucacgguacg a                                               21

<210> SEQ ID NO 57
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 57
```
ucaacaucag ucugauaagc ua                                              22

<210> SEQ ID NO 58
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 58
cgccaauauu uacgugcugc ua                                              22

<210> SEQ ID NO 59
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(24)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage
<220> FEATURE:
<221> NAME/KEY: misc_feature
<222> LOCATION: (23)..(24)
<223> OTHER INFORMATION: phosphorothioate linkage

<400> SEQUENCE: 59
aagggauucc ugggaaaacu ggac                                            24

<210> SEQ ID NO 60
<211> LENGTH: 22
<212> TYPE: RNA
<213> ORGANISM: Artificial Sequence

```
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 60
aacuauacaa ccuacuaccu ca                                              22

<210> SEQ ID NO 61
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 61
aaccacacaa ccuacuaccu ca                                              22

<210> SEQ ID NO 62
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
```

```
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 62
aaccauacaa ccuacuaccu ca                                          22

<210> SEQ ID NO 63
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: 2'-OMe modified phosphoroamidites
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(22)
<223> OTHER INFORMATION: phosphorothioate linkage

<400> SEQUENCE: 63
aacuguacaa acuacuaccu ca                                          22
```

THERAPEUTIC TARGETS AND MOLECULES

CROSS REFERENCE TO RELATED APPLICATIONS

This application is a national phase application under 35 U.S.C. §371 of International Application No. PCT/AU2008/000430, filed Mar. 26, 2008, which claims the benefit of Australian Patent Application No. 2007901595, filed Mar. 26, 2007 and U.S. Provisional Patent Application No. 60/907,208, filed Mar. 26, 2007, each of which is incorporated by reference.

FIELD OF THE INVENTION

The present invention relates generally to microRNAs (miRNAs) upregulated in allergic responses. The invention also relates to methods for the diagnosis and treatment of allergic and inflammatory conditions using these miRNAs and to methods for the treatment of allergic and inflammatory conditions using antagonists, inhibitors or supplementation of these miRNAs. Accordingly, the present invention provides miRNA signatures indicative of an allergic response and sequences of oligonucleotide antagonists of miRNAs upregulated in such a response for the treatment of allergic and inflammatory conditions. The present invention further relates to the use of miRNAs upregulated in an allergic response for the identification of novel therapeutic targets.

BACKGROUND OF THE INVENTION

Asthma is a chronic inflammatory disorder of the airways. Whilst inflammation is a natural feature in the lungs of healthy individuals, for example to effect the removal of pathogens such as bacteria and viruses and pollutants which are present in the air, in the asthmatic lung an exaggerated response occurs in response to irritants (hyperresponsiveness). Increased airway inflammation follows exposure to inducers such as allergens, viruses, exercise, or non-specific irritant inhalation. Increased inflammation leads to exacerbations characterized by shortness of breath, chest tightness, wheezing, coughing, and dyspnoea.

Asthma is the most widespread chronic health problem in the Western world and is increasing in prevalence around the world. In Australia alone, it affects over 2 million individuals. Worldwide bronchial asthma is the most common chronic disease in childhood with an overall prevalence between 5 and 20 percent across all ages. The pathogenesis is suggested to be complex and is centred on an aberrant immune response to inhalant allergens, most commonly house dust mite (HDM) allergens, that results in an inflammation of the airway wall together with an episodic constriction of the airways resulting in symptoms such as shortness of breath, wheezing, coughing, and life-threatening dyspnoea.

Current asthma therapies typically aim to reduce the inflammatory process by suppressing the expression of steroid-sensitive proteins via systemic or local application of corticosteroids, by inhibiting the action of leukotrienes via systemic application of leukotriene receptor/leukotriene antagonists, or by neutralising immunoglobulin E (IgE) or interleukin-5 (IL-5) via systemic application of antibodies directed against these molecules (these therapies are commonly referred as "preventers"). Alternative current therapies aim to inhibit the constriction of airways by stimulating beta-2 receptors in the airways via short or long-acting beta-2 receptor agonists ("relievers" and "controllers" respectively).

However these existing therapies do not address the complex nature of the pathways that are activated in the airways during asthma on a molecular level. Rather they aim to either suppress only one or a few out of numerous disease mechanisms that promote aberrant immune responses or alleviate symptoms only. Furthermore current therapies are commonly associated with significant side effects (for example in the case of steroid use) or tachyphylaxis (for example following administration of long-acting beta-2 receptor antagonists).

Accordingly, there remains a clear need for the development of effective therapies for the treatment of inflammatory conditions such as asthma. There is also an ongoing need to pursue asthma-related research at the level of both understanding underlying causative factors, identifying novel therapeutic targets and developing new treatment, regimens, which can contribute to expanding the existing range of therapeutic and prophylactic treatments available.

MicroRNAs (miRNAs) are an abundant class of small endogenous non-coding RNA molecules that have been highly conserved through evolution. Indeed, in mammalian species, 100% conservation of many miRNA sequences is observed between humans and mice. More than 1000 miRNAs have been identified to date, and approximately 400 miRNAs with known sequence have been found in humans. miRNAs are believed to play an important role in regulating gene expression. Each miRNA binds incompletely to its cognate target messenger RNA (mRNA) and as such each miRNA may bind to and potentially regulate many target mRNAs. Computational analysis suggests that there may be several hundred mRNA targets for any given miRNA. Accordingly, a unique miRNA may regulate the expression of several hundred mRNAs each of which codes for a specific protein. It is suggested that miRNAs may regulate the expression of up to one third of all human genes that code for an unique protein.

Mature miRNAs are derived from so-called pri-miRNAs that are transcribed from regions of non-coding DNA. Pri-miRNAs, usually containing several hundred nucleotides, are processed into stem-loop precursors (pre-miRNAs) of approximately 70 nucleotides by RNase III endonuclease. Pre-miRNAs are actively transported into the cytoplasm where they are further processed into short RNA duplexes, typically of 21-23 bp. The functional miRNA strand dissociates from its complementary non-functional strand and locates within the RNA-induced-silencing-complex (RISC). (Alternatively, RISC can directly load pre-miRNA hairpin structures.) The miRNA-RISC complex incompletely binds to its cognate mRNA target through a small region at the 5' end. miRNA-induced regulation of gene expression is then typically achieved by translational repression, either degrading proteins as they emerge from ribosomes or 'freezing' ribosomes, and/or promoting the movement of target mRNAs into sites of RNA destruction.

The roles of miRNAs have yet be completely elucidated. However they appear to be important in a number of developmental processes, for example in differentiation and maintenance of cellular identity in hematopoiesis, in establishing muscle phenotypes, in morphogenesis of epithelial tissues, organogenesis and in other metabolic processes. Additionally, specific miRNAs are increasingly being implicated in disease conditions, including cancers such as chronic lymphocytic leukemia (Calin, G. A. et al., 2005, *N Engl J Med* 354:524-525).

The present invention is predicated on the inventors' surprising finding that expression of a subset of miRNAs is upregulated or downregulated in response to allergen challenge and the finding that a modified antisense oligonucleotide specific for an upregulated miRNA is able to suppress hallmark features of allergic airways disease. Accordingly, the present invention opens avenues for novel therapeutic approaches to the treatment of allergic and inflammatory disorders.

SUMMARY OF THE INVENTION

The present invention provides, inter alia, methods for the treatment and/or prophylaxis of inflammation or an inflammatory condition in a subject, said methods comprising regulating the level of expression of one or more miRNA in airway tissue or cells residing in the lung of said subject, wherein altered regulation of an miRNA selected from hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021, ambi_miR_7008, hsa_miR_24, hsa_miR_30c, hsa_miR_25, hsa_miR_15b, hsa_miR_181b, hsa_miR_150, hsa_miR_361, hsa_miR_345, ambi_miR_7031, relative to normal endogenous levels, reduces or prevents an inflammatory or allergic response.

According to a first aspect of the present invention there is provided a method for treating or preventing inflammation or an inflammatory condition in a subject, the method comprising administering to the subject an effective amount of at least one miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008.

The miRNA may comprise a nucleotide sequence as set forth in any one of SEQ ID Nos: 1 to 27.

The inflammation may be allergic inflammation. The inflammatory condition may be characterised by or associated with allergic inflammation. The inflammatory condition may be selected from asthma, chronic obstructive pulmonary disease, allergic rhinitis, eosinophilic bronchitis, and conditions characterised by or associated with inflammation of tissues and joints. In a particular embodiment the condition is asthma.

According to a second aspect of the present invention there is provided use of an miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008 as an anti-inflammatory agent.

According to a third aspect of the present invention there is provided a pharmaceutical composition for the treatment of prevention of inflammation or an inflammatory condition, the composition comprising at least one miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008.

According to a fourth aspect of the present invention there is provided the use of at least one miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008, for the manufacture of a medicament for the treatment or prevention of inflammation or an inflammatory condition.

According to a fifth aspect of the present invention there is provided a method for treating or, preventing inflammation or an inflammatory condition in a subject, the method comprising administering to the subject an effective amount of at least one antagonist of one or more miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021 and ambi_miR_7008.

The miRNA may comprise a nucleotide sequence as set forth in any one of SEQ ID Nos: 1 to 15 or 24 to 27.

In one embodiment the antagonist is an oligonucleotide. The oligonucleotide may be an RNA oligonucleotide. The oligonucleotide may comprise a nucleotide sequence as set forth in any one of SEQ ID Nos:28 to 42 or 51 to 54. The oligonucleotide sequence may comprise one or more modifications such as non-naturally occurring nucleotide analogues, non-phosphate linkages between nucleotides, and/or conjugated moieties. By way of example, one or more of the nucleotides in the oligonucleotide sequence may be a modified nucleotide such as a 2'-OMe-modified nucleotide. Alternatively, or in addition, the oligonucleotide sequence may include, for example, phosphorothioate linkages between one or more nucleotides in the sequence. The oligonucleotide sequence may be conjugated atone or both ends to a suitable moiety, such as a cholesterol moiety linked via a hydroxyprolinol linkage.

In one embodiment the miRNA is hsa_miR_126. In one embodiment the miRNA is hsa_miR_126 and the antagonist comprises the sequence:

```
                                            (SEQ ID NO: 56)
5'-mG.*.mC.*.mA.mU.mU.mA.mU.mU.mA.mC.mU.mC.mA.mC.

mG.mG.mU.mA.*.mC.*.mG.*.mA.*.-3'-Chl,
``` where m=2'-OMe modified phosphoramidite, *=a phosphorothioate linkage, and -Chl=hydroxyprolinol linked cholesterol.

The inflammation may be allergic inflammation. The inflammatory condition may be characterised by or associated with allergic inflammation. The inflammatory condition may be selected from asthma, chronic obstructive pulmonary disease, allergic rhinitis, eosinophilic bronchitis, and conditions characterised by or associated with inflammation of tissues and joints. In a particular embodiment the condition is asthma.

According to a sixth aspect of the present invention there is provided a pharmaceutical composition for the treatment of prevention of inflammation or an inflammatory condition, the composition comprising at least one antagonist of one or more miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021 and ambi_miR_7008.

According to a seventh aspect of the present invention there is provided the use of an antagonist of one or more miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021 and ambi_miR_7008, for the manufacture of a medicament for the treatment or prevention of inflammation or an inflammatory condition.

According to an eighth aspect of the present invention there is provided an antisense construct specific for an miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008. The miRNA may comprise a nucleotide sequence as set forth in any one of SEQ ID Nos:1 to 27.

In one embodiment the antisense construct is an oligonucleotide complementary to one of said miRNAs. The oligonucleotide may comprise a nucleotide sequence as set forth in any one of SEQ ID NOs:28 to 54.

According to a ninth aspect of the present invention there is provided a method for treating or preventing inflammation or an inflammatory condition in a subject, the method comprising administering to the subject an effective amount of at least one oligonucleotide according to the eighth aspect.

According to a tenth aspect of the present invention there is provided a pharmaceutical composition for the treatment of prevention of an inflammatory condition, the composition comprising at least one oligonucleotide according to the eighth aspect.

According to an eleventh aspect of the present invention there is provided the use of an miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008, for the identification of molecules bound by or regulated by said miRNA, wherein the activity or expression of said molecules is associated with inflammation, an inflammatory condition, and/or an allergic response.

According to a twelfth aspect of the present invention there is provided a method for diagnosing an inflammatory condition in a subject, the method comprising:
(a) obtaining a biological sample from the subject; and
(b) determining the level of expression of at least one miRNA selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, hsa_miR_24, hsa_miR_30c, hsa_miR_25, hsa_miR_15b, hsa_miR_181b, hsa_miR_150, hsa_miR_361, hsa_miR_345, ambi_miR_7031, mmu_miR_294, hsa_miR_136, ambi_miR_7065, ambi_miR_7099, hsa_miR_181a, mmu_miR_325, ambi_miR_7021 and ambi_miR_7008 in the sample,
wherein the level of expression of the at least one miRNA is indicative of an inflammatory condition in the subject.

According to a further aspect of the present invention there is provided a method for inducing asthma or a condition associated therewith, such as eosinophilia, the method comprising administering to a subject an effective amount of an antagonist of one or more miRNA selected from the group consisting of: hsa_miR_24, hsa_miR_23a, hsa_miR_30c, hsa_miR_25, hsa_miR_15b, hsa_miR_181b, hsa_miR_150, hsa_miR_361, hsa_miR_345 and ambi_miR_7031.

According to a further aspect of the present invention there is provided a method for identifying a molecule or compound that binds to an miRNA as disclosed herein, the method comprising the steps of: (a) contacting a candidate molecule or compound with the miRNA; and (b) assaying for the formation of a complex between the candidate molecule or compound and the miRNA.

According to yet a further aspect of the invention there is provided a method of screening for a molecule or compound the expression and/or activity of which is regulated by an miRNA as disclosed herein, the method comprising the steps of: (a) contacting the miRNA with a candidate molecule or compound under conditions suitable to enable interaction of the candidate to the miRNA (either direct or indirect); and (b) assaying for expression and/or activity of the candidate molecule or compound.

BRIEF DESCRIPTION OF THE DRAWINGS

The present invention will now be described, by way of non-limiting example only, with reference to the accompanying drawings.

Figure 1:
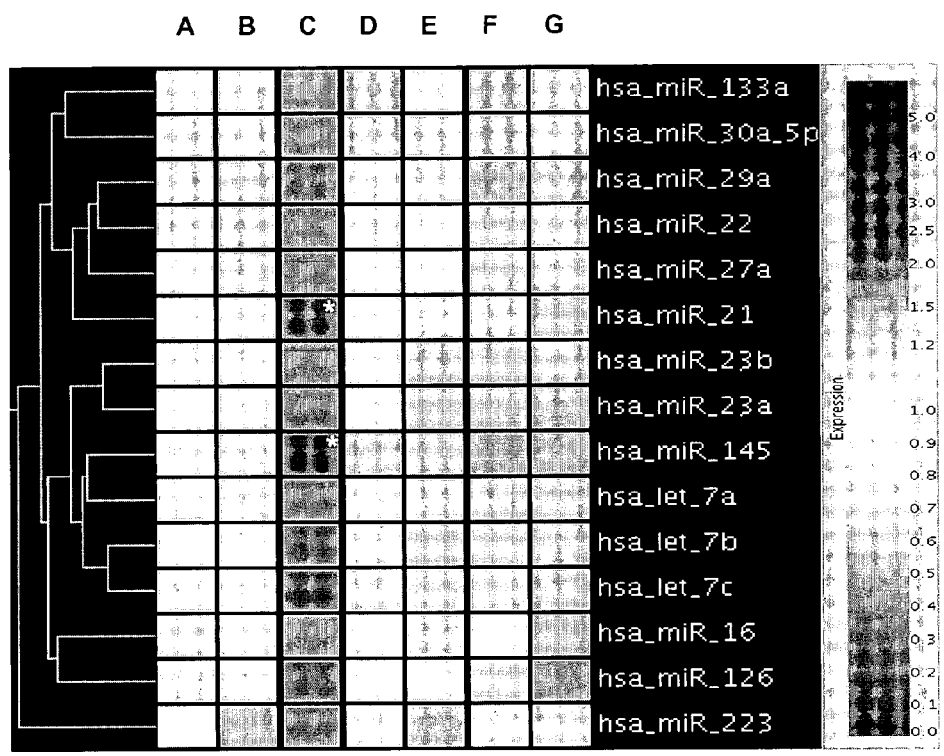
FIG. 1. miRNA signature in mouse airway wall after a single intra-tracheal challenge with house dust mite (HDM) allergen. Intensity of shading indicates level of expression of individual miRNA species indicated following HDM allergen challenge relative to saline only challenge. A, B, C: 2 hrs, 8 hrs, 24 hrs respectively after house dust mite allergen challenge; D, E, F: 2 hrs, 8 hrs, 24 hrs after treatment with saline; G: no challenge (negative control). Each group is representative of the mean expression levels from 2 mice. Shown are those miRNA displaying 1.5-fold or greater increase in expression following HDM allergen challenge relative to saline challenge. Asterisk (*) indicates miRNA species displaying greater than 2-fold increase in expression (hsa_miR_145, 2.2-fold; and hsa_miR_21, 2.3-fold).
Figure 2:
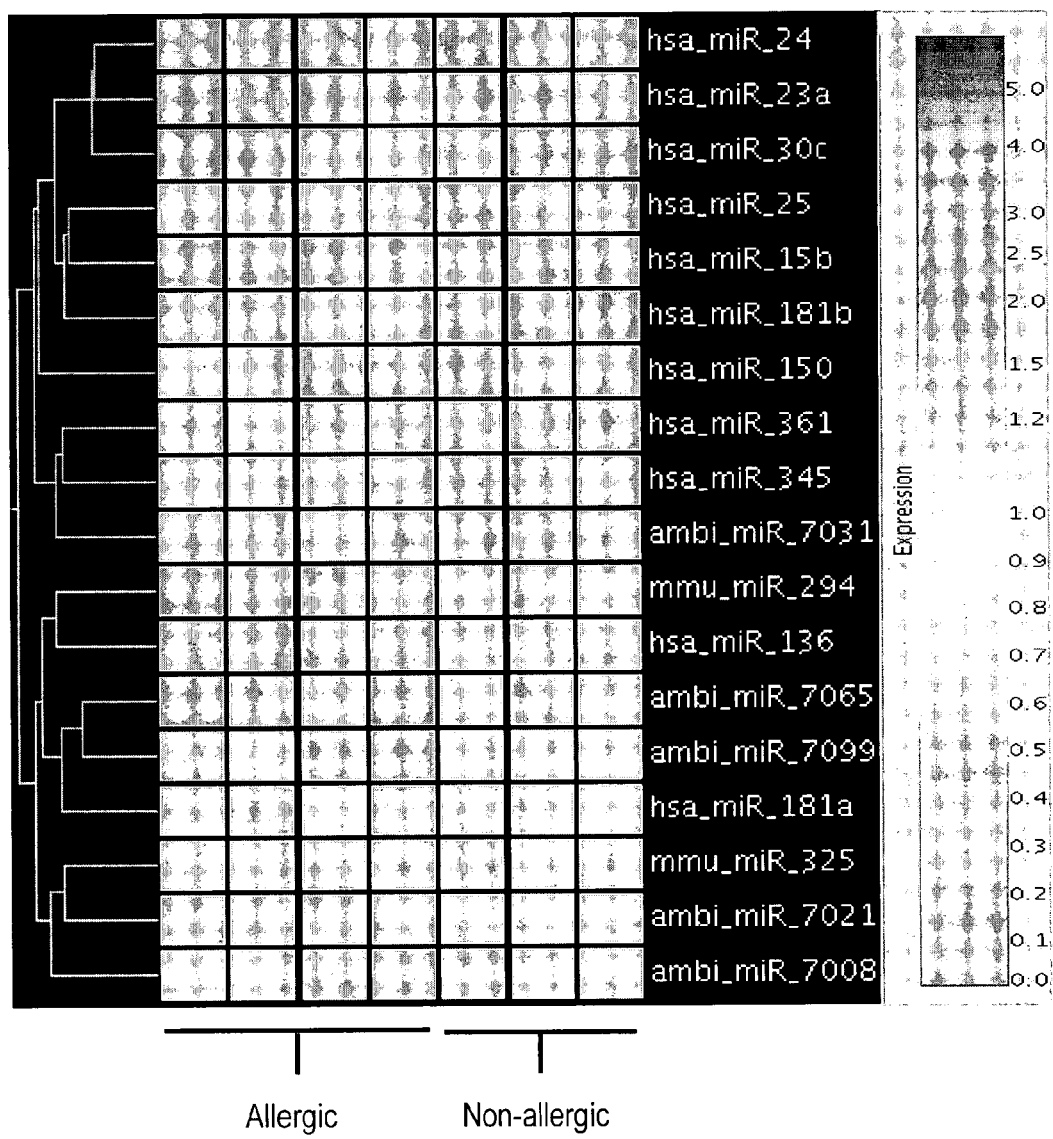
FIG. 2. miRNA signature in mouse whole lung of ovalbumin (OVA) sensitised and re-challenged mice (allergic) and mice treated with saline (non-allergic). Intensity of shading indicates level of expression of individual miRNA species indicated following OVA challenge relative to saline only challenge. Each column is representative of one mouse. 18 miRNAs were differentially expressed between allergic and non-allergic mice in the lung (p<0.05). hsa_miR_24, hsa_miR_23a, hsa_miR_30c, hsa_miR_25, hsa_miR_15b, hsa_miR_181b, hsa_miR_150, hsa_miR_361, hsa_miR_345, and ambi_miR_7031 were down-regulated in OVA sensitised/challenged mice, whilst mmu_miR_294, hsa_miR_136, ambi_miR_7065, ambi_miR_7099, hsa_miR_181a, mmu_miR_325, ambi_miR_7021 and ambi_miR_7008 were upregulated.

The nucleotide sequences of miRNA described herein are set forth in SEQ ID NOs:1 to 27 and 55. Nucleotide sequences of antisense oligonucleotides complementary to the miRNA sequences of SEQ ID NOs: 1 to 27 are set forth in SEQ ID NOs:28 to 54. The sequences of antisense oligonucleotides Ant 126 and Ant 21 are set forth in SEQ ID NOs:56 and 57 respectively.

DETAILED DESCRIPTION OF THE INVENTION

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

In the context of this specification, the term "antagonist" refers to any agent capable of inhibiting the expression or activity of an miRNA. Thus, the antagonist may operate to prevent transcription or post-transcriptional processing of the miRNA or otherwise inhibit the activity of the miRNA in any way, via either direct or indirect action. The antagonist may for example be nucleic acid, peptide, any other suitable chemical compound or molecule or any combination of these. Additionally, it will be understood that in indirectly impairing the activity of the miRNA, the antagonist may effect the activity of other cellular molecules which may in turn act as regulators of the expression of activity of the miRNA itself. Similarly, the antagonist may effect the activity of molecules which are themselves subject to regulation or modulation by the miRNA.

It will be understood that as used herein the term "expression" may refer to expression of a polypeptide or protein, or to expression of a polynucleotide or gene, depending on the context. The polynucleotide may be coding or non-coding (e.g. miRNA). Expression of a polynucleotide may be determined, for example, by measuring the production of RNA transcript levels. Expression of a protein or polypeptide may be determined, for example, by immunoassay using an antibody(ies) that bind with the polypeptide.

In the context of this specification, the term "activity" as it pertains to a protein, polypeptide or polynucleotide means any cellular function, action, effect or influence exerted by the protein, polypeptide or polynucleotide, either by a nucleic acid sequence or fragment thereof, or by the protein or polypeptide itself or any fragment thereof.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated. Polynucleotides may be chemically modified by a variety of means known to those skilled in the art.

As used herein the term "oligonucleotide" refers to a single-stranded sequence of ribonucleotide or deoxyribonucleotide bases, known analogues of natural nucleotides, or mixtures thereof. An oligonucleotide predominantly comprising ribonucleotide bases, natural or non-natural, may be referred to as an RNA oligonucleotide. Oligonucleotides are typically short (for example less than 50 nucleotides in length) sequences which may be prepared by any suitable method, including, for example, direct chemical synthesis or cloning and restriction of appropriate sequences. "Antisense oligonucleotides" are oligonucleotides complementary to a specific DNA or RNA sequence. Typically in the context of the present invention an antisense oligonucleotide is an RNA oligonucleotide complementary to a specific miRNA. The antisense oligonucleotide binds to and silences or represses, partially of fully, the activity of its complementary miRNA. Not all bases in an antisense oligonucleotide need be complementary to the 'target' or miRNA sequence; the oligonucleotide need only contain sufficient complementary bases to enable the oligonucleotide to recognise the target. An oligonucleotide may also include additional bases. The antisense oligonucleotide sequence may be an unmodified ribonucleotide sequence or may be chemically modified or conjugated by a variety of means as described herein.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "subject" as used herein refers to mammals and includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal. Even more preferably, the mammal is a human.

As exemplified herein the inventors' investigated whether miRNAs are expressed at altered levels in the airways and cells residing in the lung where an aberrant immune response together with inflammation has been induced by direct exposure to allergen, all of which are the hallmark features of bronchial asthma. The present invention is predicated on the inventors' findings, as disclosed herein, of specific miRNAs the expression of which is upregulated or downregulated in response to allergen exposure and the finding that antisense oligonucleotides directed against upregulated miRNA suppress features that are characteristic of diseases such as bronchial asthma. These findings offer new therapeutic targets for the treatment of inflammatory conditions, in particular allergic airways diseases.

The group of miRNA determined herein to be upregulated during an allergic inflammatory response include: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021 and ambi_miR_7008.

Those miRNA found to be downregulated during an allergic inflammatory response include: hsa_miR_24, hsa_miR_30c, hsa_miR_25, hsa_miR_15b, hsa_miR_181b, hsa_miR_150, hsa_miR_361, hsa_miR_345, ambi_miR_7031.

Embodiments of the invention relate to methods for treating a subject having an inflammatory condition or at risk of developing such a condition. In these embodiments, the miRNAs disclosed herein, or antagonists thereto can act as novel therapeutic or prophylactic agents. Typically, methods comprise administering a pharmaceutical composition of the invention to the patient, such that expression of one or more specific miRNAs is either upregulated or down-regulated.

Accordingly, one aspect of the present invention provides a method for the treatment or prevention of an inflammatory condition in a subject, the method comprising administering to the subject an effective amount of one or more of the above listed miRNA. Without wishing to be bound by theory, the inventors suggest that at least some of those miRNA the expression of which is upregulated during an allergic inflammatory response may act as transcriptional suppressors activated in response to a stimulus (e.g. allergen) that then play a role in suppressing the response directly at the level of target genes or by producing factors that act to suppress the response via another mechanism. Thus administering such miRNA may have the desired therapeutic effect by, for example, functional antagonism.

A further aspect of the invention provides a method for the treatment or prevention of an inflammatory condition in a subject, the method comprising administering to the subject an effective amount of at least one antagonist of one or more miRNA the expression of which is upregulated during an allergic inflammatory response. Suitable miRNA targets are selected from the group consisting of: hsa_miR_16, hsa_miR_21, hsa_miR_145, hsa_miR_126, hsa_miR_133a, hsa_miR_30a_5p, hsa_miR_29a, hsa_miR_22, hsa_miR_27a, hsa_miR_23a, hsa_miR_23b, hsa_miR_223, hsa_let_7a, hsa_let_7b, hsa_let_7c, mmu_miR_294, hsa_miR_136, ambi_miR_7065, ambi_miR_7099, hsa_miR_181a, mmu_miR_325, ambi_miR_7021 and ambi_miR_7008.

The nucleotide sequences of the human (hsa) and mouse (mmu) miRNA to which the present invention relates are shown in SEQ ID NOs:1 to 27. Additional sequence information for these miRNA, including genomic location, can be found at the publically accessible miRBase database. Also disclosed herein is the association with allergic inflammation of a series of novel miRNA ("ambi" miRNAs) from mirVana miRNA Bioarrays (Ambion, Inc.), the sequences of which are not publicly available.

The invention also provides antagonists of these miRNA. Those skilled in the art will readily appreciate that suitable antagonists for use in accordance with the invention may take a variety of forms. Typically the antagonist will be an antisense construct comprising a nucleotide sequence specific to an miRNA of the invention, or a portion thereof, wherein the antisense construct inhibits, at least partially, the activity of the miRNA. By "specific" it is meant that the antisense construct is substantially specific for the miRNA, but not necessarily exclusively so. That is, while being specific for a particular miRNA sequence, the antisense construct may also cross-hybridise with other sequences, such as other miRNA sufficient to inhibit expression. Further, for example, the nucleotide sequence of an antisense construct according to the present invention may display less than 100% sequence identity with a particular miRNA and retain specificity thereto. It will be appreciated by those skilled in the art that suitable antisense constructs need not bind directly with the miRNA to which they are directed in order to effect the activity of those miRNA. Binding of an antisense construct to its complementary cellular nucleotide sequence may interfere with transcription, RNA processing, transport, and/or stability of the miRNA to which it is specific.

Suitable antisense constructs for use in accordance with the present invention include antisense oligonucleotides, small interfering RNAs (siRNAs) and catalytic antisense nucleic acid constructs. Suitable antisense oligonucleotides may be prepared by methods well known to those of skill in the art. Typically oligonucleotides will be chemically synthesized on automated synthesizers. By way of non-limiting example, the sequences of particular oligonucleotides specific for miRNA disclosed herein are shown in SEQ ID Nos: 28 to 54. The miRNA to which these oligonucleotides are specific are shown in Table 1 below.

TABLE 1

Sequences of miRNA and corresponding antisense oligonucleotides.
SEQ ID NO

| miRNA | Antisense oligo |
|---|---|
| 1 | 28 |
| 2 | 29 |
| 3 | 30 |

TABLE 1-continued

Sequences of miRNA and corresponding antisense oligonucleotides.
SEQ ID NO

| miRNA | Antisense oligo |
|---|---|
| 4 | 31 |
| 5 | 32 |
| 6 | 33 |
| 7 | 34 |
| 8 | 35 |
| 9 | 36 |
| 10 | 37 |
| 11 | 38 |
| 12 | 39 |
| 13 | 40 |
| 14 | 41 |
| 15 | 42 |
| 16 | 43 |
| 17 | 44 |
| 18 | 45 |
| 19 | 46 |
| 20 | 47 |
| 21 | 48 |
| 22 | 49 |
| 23 | 50 |
| 24 | 51 |
| 25 | 52 |
| 26 | 53 |
| 27 | 54 |

These exemplary oligonucleotides are 100% complementary to their respective miRNAs, although those skilled in the art will readily appreciate that one or more base changes may be made such that less than 100% complementarity exists whilst the oligonucleotide retains specificity for its miRNA and retains antagonistic activity against this miRNA. Further, as described below, oligonucleotide sequences may include one or more chemical modifications without departing from the scope of the present invention.

Oligonucleotides in accordance with the invention may include modifications designed to improve their delivery into cells, their stability once inside a cell, and/or their binding to the appropriate miRNA target. For example, the oligonucleotide sequence may be modified by the addition of one or more phosphorothioate (for example phosphoromonothioate or phosphorodithioate) linkages between residues in the sequence, or the inclusion of one or morpholine rings into the backbone. Alternative non-phosphate linkages between residues include phosphonate, hydroxylamine, hydroxylhydrazinyl, amide and carbamate linkages (see, for example, United States Patent Application Publication No. 20060287260, Manoharan I., the disclosure of which is incorporated herein in its entirety), methylphosphonates, phosphorothiolates, phosphoramidates or boron derivatives. The nucleotide residues present in the oligonucleotide may be naturally occurring nucleotides or may be modified nucleotides. Suitable modified nucleotides include 2'-O-methyl nucleotides, such as 2'-O-methyl adenine, 2'-O-methyl-uracil, 2'-O-methyl-thymine, 2'-O-methyl-cytosine, 2'-O-methyl-guanine, 2'-O-methyl-2-amino-adenine; 2-amino-adenine, 2-amino-purine, inosine; propynyl nucleotides such as 5-propynyl uracil and 5-propynyl cytosine; 2-thio-thymidine; universal bases such as 5-nitro-indole; locked nucleic acid (LNA), and peptide nucleic acid (PNA). The ribose sugar moiety that occurs naturally in ribonucleosides may be replaced, for example with a hexose sugar, polycyclic heteroalkyl ring, or cyclohexenyl group as described in United States Patent Application Publication No. 20060035254, Manoharan et al., the disclosure of which is incorporated herein in its entirety. Alternatively, or in addition, the oligonucleotide sequence may be conjugated to one or more suitable chemical moieties at one or both ends. For example, the oligonucleotide may be conjugated to cholesterol via a suitable linkage such as a hydroxyprolinol linkage at the 3' end.

The synthesis of oligonucleotide with 'silencing' activity against specific miRNA, including the miRNA hsa_miR_16 disclosed herein, is described in Krutzfeldt, J. et al., 2005, Nature 438:685-689, the disclosure of which is incorporated herein in its entirety. In this Krutzfeldt et al. the sequence of a modified oligonucleotide ("antagomir") against hsa_miR_16 was disclosed as follows:

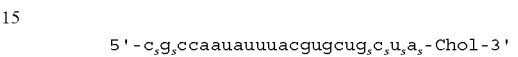

wherein the lower case letters represent 2-O-methyl nucleotides, subscript 's' represents a phosphorothioate linkage and 'Chol' represents a conjugated cholesterol moeity via a hydroxyprolinol linkage at the 3' end. Embodiments of the present invention contemplate use of this specific "antagomir" sequence as well as modifications or variations thereof. Similarly, oligonucleotides against other miRNA disclosed herein may be designed so as to contain corresponding non-natural modifications. The design of such oligonucleotides or antagomirs for use in accordance with the invention is well within the capabilities of those skilled in the art.

By way of example, modified antisense oligonucleotides (antagomirs) directed against particular miRNAs as disclosed herein are shown below (where m=2'-OMe modified phosphoramidite, *=phosphorothioate linkage, and -Chl=hydroxyprolinol linked cholesterol). These sequences are examples of suitable antisense molecules only and those skilled in the art will readily appreciate that alterations and modifications may be made thereto without departing from the invention.

```
Antagomir to miR_16
5'mC.*.mG.*.mC.mC.mA.mA.mU.mA.mU.mU.mU.mA.mC.mG.

mU.mG.mC.mU.mG.*.mC.*.mU.*.mA.*.3'-Chl

Antagomir to miR_145
5'mA.*.mA.*.mG.mG.mG.mA.mU.mU.mC.mC.mU.mG.mG.mG.

mA.mA.mA.mA.mC.mU.mG.*.mG.*.mA.*.mC.*.3'-Chl

Antagomir to let_7a
5'mA.*.mA.*.mC.mU.mA.mU.mA.mC.mA.mA.mC.mC.mU.mA.

mC.mU.mA.mC.mC.*.mU.*.mC.*.mA.*.3'-Chl

Antagomir to let_7b
5'mA.*.mA.*.mC.mC.mA.mC.mA.mC.mA.mA.mC.mC.mU.mA.

mC.mU.mA.mC.mC.*.mU.*.mC.*.mA.*.3'-Chl

Antagomir to let_7c
5'mA.*.mA.*.mC.mC.mA.mU.mA.mC.mA.mA.mC.mC.mU.mA.

mC.mU.mA.mC.mC.*.mU.*.mC.*mA.*.3'-Chl

Antagomir to let_7g
5'mA.*.mA.*.mC.mU.mG.mU.mA.mC.mA.mA.mA.mC.mU.mA.

mC.mU.mA.mC.mC.*.mU.*.mC.*.mA.*.3'-Chl

Antagomir to miR_126
```

-continued (SEQ ID NO: 56)
> 5'mG.*.mC.*.mA.mU.mU.mA.mU.mU.mA.mC.mU.mC.mA.mC.

mG.mG.mU.mA.*.mC.*.mG.*.mA.*.3'-Chl

Antagomir to miR_21

(SEQ ID NO: 57)
5'mU.*.mC.*.mA.mA.mC.mA.mU.mC.mA.mG.mU.mC.mU.mG.

mA.mU.mA.mA.mG.*.mC.*.mU.*.mA.*.3'-Chl

As exemplified herein, modified oligonucleotides directed against hsa_miR_126 and hsa_miR_21, with the sequences shown in SEQ ID Nos:56 and 57, are capable of inhibiting expression of these miRNA in vivo. Further, administration of the modified oligonucleotide directed against hsa_miR_126 results in a reduction in IL-5 release, a reduction in eosinophil numbers and a reduction in airway hyperreactivity. These findings clearly demonstrate the efficacy of antisense oligonucleotides directed against specific miRNAs in treating allergic and inflammatory diseases such as asthma.

An alternative antisense technology, known as RNA interference (RNAi), see, eg. Chuang et al. (2000) *PNAS USA* 97: 4985) may be used, according to known methods in the art (for example Fire et al. (1998) *Nature* 391: 806-811; Hammond, et al. (2001) *Nature Rev, Genet.* 2: 110-1119; Hammond et al. (2000) *Nature* 404: 293-296; Bernstein et al. (2001) *Nature* 409: 363-366; Elbashir et al (2001) *Nature* 411: 494-498; WO 99/49029 and WO 01/70949, the disclosures of which are incorporated herein by reference), to inhibit the expression or activity of miRNA. RNAi refers to a means of selective post-transcriptional gene silencing by destruction of specific RNA by small interfering RNA molecules (siRNA). The siRNA is generated by cleavage of double stranded RNA, where one strand is identical to the message to be inactivated. Double-stranded RNA molecules may be synthesised in which one strand is identical to a specific region of the miRNA transcript and introduced directly. Alternatively corresponding dsDNA can be employed, which, once presented intracellularly is converted into dsRNA. Methods for the synthesis of suitable molecules for use in RNAi and for achieving post-transcriptional gene silencing are known to those of skill in the art.

A further means of inhibiting the expression or activity of miRNA to which the invention relates may be achieved by introducing catalytic antisense nucleic acid constructs, such as ribozymes, which are capable of cleaving miRNA transcripts. Ribozymes are targeted to and anneal with a particular sequence by virtue of two regions of sequence complementarity to the target flanking the ribozyme catalytic site. After binding the ribozyme cleaves the target in a site-specific manner. The design and testing of ribozymes which specifically recognise and cleave miRNA sequences can be achieved by techniques well known to those in the art (for example Lieber and Strauss, (1995) *Mol. Cell. Biol.* 15:540-551, the disclosure of which is incorporated herein by reference).

Embodiments of the present invention relate to the use of antagonists of miRNAs disclosed herein for the treatment or prevention of inflammation or inflammatory conditions. Typically the inflammatory conditions are characterised by or otherwise associated with allergic inflammation. Suitable inflammatory conditions to which the present invention include, but are not limited to, asthma, chronic obstructive pulmonary disease, allergic rhinitis, eosinophilic bronchitis and other conditions characterised by or associated with inflammation of tissues and joints. Further, by virtue of potential negative feedback regulation, the invention also contemplates the use of miRNAs disclosed herein as anti-inflammatory agents and thus in the treatment or prevention of inflammation or inflammatory conditions. In the case of antagonists, such agents may be administered to subjects in order to inhibit miRNA activity and/or expression. Both miRNA and antagonists thereof may be administered in accordance with the invention in the form of a composition comprising the agent(s) together with one or more pharmaceutically acceptable carriers, diluents and/or excipients.

It will be understood that the specific dose level of a composition of the invention for any particular individual will depend upon a variety of factors including, for example, the activity of the specific agents employed, the age, body weight, general health and diet of the individual to be treated, the time of administration, rate of excretion, and combination with any other treatment or therapy. Single or multiple administrations can be carried out with dose levels and pattern being selected by the treating physician.

According to embodiments of the invention, miRNA and antagonists thereof may be administered in any suitable form. In accordance with the present invention active agents are typically administered in the form of pharmaceutical compositions, which compositions may comprise one or more pharmaceutically acceptable carriers, excipients or diluents. Such compositions may be administered in any convenient or suitable route such as by parenteral, oral, nasal or topical routes, for example by inhalation, and thus may be formulated in a variety of forms suitable for the chosen route of administration, for example as capsules, tablets, caplets, elixirs for oral ingestion, in an aerosol form suitable for administration by inhalation, such as by intranasal inhalation or oral inhalation, ointment, cream or lotion suitable for topical administration, or in an injectible formulation suitable for parenteral administration, that is, subcutaneous, intramuscular or intravenous injection.

For example, miRNA and antagonists thereof may be administered in accordance with the invention as liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference. The agents may also be administered in the form of microparticles. For example, biodegradable microparticles formed from polylactide (PLA), polylactide-co-glycolide (PLGA), and epsilon-caprolactone (ε-caprolactone) may be used.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for parenteral administration, or in the form of a formulation suitable for oral ingestion (such as capsules, tablets, caplets, elixirs, for example).

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration. Adjuvants typically include emollients, emulsifiers, thickening agents, preservatives, bactericides and buffering agents. For administration as an injectable solution or suspension, non-toxic parenterally acceptable diluents or carriers can include, Ringer's solution, isotonic saline, phosphate buffered saline, ethanol and 1,2 propylene glycol.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The invention also contemplates encapsulated formulations to protect polynucleotide and oligonucleotide agents against rapid elimination from the body, such as via controlled release formulations and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In alternative embodiments of the invention miRNA and antisense constructs such as antisense oligonucleotides may be administered to the subject in need thereof in a vector. The vector may be a plasmid vector, a viral vector, or any other suitable vehicle adapted for the insertion and foreign sequences and introduction into eukaryotic cells. Preferably the vector is an expression vector capable of directing the transcription of the DNA sequence of an antisense molecule of the invention into RNA. Preferred viral expression vectors include for example epstein-barr virus-, bovine papilloma virus-, adenovirus- and adeno-associated virus-based vectors. In a particular embodiment, the vector is episomal. The use of a suitable episomal vector provides a means of maintaining the antisense molecule in the required target cells in high copy number extra-chromosomally thereby eliminating potential effects of chromosomal integration.

In treating or preventing inflammation and inflammatory conditions, the present invention contemplates the administration of multiple miRNA and/or multiple miRNA antagonists. Whether it is suitable or desirable to administer one or more miRNA, one or more miRNA antagonists or optionally both miRNA and miRNA antagonists can be determined by those skilled in the art on a case-by-case basis. The invention also contemplates combination therapies, wherein agents as described herein are coadministered with other suitable agents which may facilitate the desired therapeutic or prophylactic outcome. For example, in the context of asthma, one may seek to maintain ongoing anti-inflammatory therapies in order to control the incidence of inflammation whilst employing agents in accordance with embodiments of the present invention. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

The present invention also relates to the use of miRNAs disclosed herein for the diagnosis of, or determination of predisposition to, inflammatory conditions. Accordingly, an aspect of the invention provides a method for diagnosing an inflammatory condition in a subject, or determining the predisposition of a subject to an inflammatory condition, the method comprising:

(a) obtaining a biological sample from the subject; and (b) determining the level of expression of at least one miRNA selected from the group consisting of: in the sample, wherein the level of expression of the at least one miRNA is indicative of an inflammatory condition, or a predisposition thereto, in the subject.

miRNA and antagonists thereof as described herein may also be used for the screening and identification of molecules and compounds that interact with the miRNA of the invention, including endogenous nucleic acid and polypeptide targets of these miRNA. Such targets may be regulated by the miRNA of the invention, may regulate the miRNA of the invention and/or may exert an effect on other cellular molecules or processes involved in allergic inflammatory responses. Thus, such molecules and compounds may offer novel therapeutic targets. By "regulate" is meant regulation or modulation (either positive or negative) of activity or expression. Thus, for example, a molecule or compound may induce, promote, activate, increase, inhibit or prevent activity or expression of another molecule(s) or compound(s). Suitable molecules and compounds may exert their effect on by virtue of either a direct (for example binding) or indirect interaction. Molecules and compounds which bind, or otherwise interact with, miRNA of the invention may be identified by a variety of suitable methods known to those skilled in the art.

The present invention also provides kits for use in accordance with methods of the invention. For example, kits of the invention may contain oligonucleotides representing the miRNAs disclosed herein and/or antagonists thereof, such as antisense molecules specific for these miRNA. Such kits may be used, for example, to detect the presence of miRNAs in a biological sample and/or detect molecular targets or binding partners of such miRNA. Detection using such kits is useful for a variety of purposes, including but not limited to disease diagnosis, epidemiological studies and performing screening methods of the present invention. Additionally, kits may contain means for detecting the binding of an miRNA of the invention to a binding partner. For example oligonucleotides may be conjugated to a detectable substrate such as a fluorescent, radioactive or luminescent compound, enabling their detection in assays known to those skilled in the art. Kits according to the present invention may also include other components required to conduct the methods of the present invention, such as buffers and/or diluents. The kits typically include containers for housing the various components and instructions for using the kit components in the methods of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

Example 1 miRNA Expression in House Dust Mite (HDM) Allergen Challenged Mice

Example 1A miRNA Expression Following a Single HDM Allergen Challenge

To determine whether miRNA concentrations increase in the airways in response to direct exposure to an allergen that results in an aberrant immune response and inflammation, the airways of BALB/c mice were exposed to HDM allergen in the form of a commercially available HDM extract (Greer Laboratories Inc., USA; supplied by Dermcare Vet Pty Ltd, Australia). Mice were separated into two groups (n=6 in each group). The first group was challenged with 50 μl HDM extract (50 μg dissolved in 50 μl saline) by intratracheal instillation and the second group challenged with 50 μl of 0.9% saline by intratracheal instillation. In the HDM and saline treated groups, mice (n=2) were sacrificed at 2 hrs, 8 hrs and 24 hrs following treatment. A further group (naïve) was unchallenged (n=2).

To isolate miRNAs lung parenchyma was carefully removed from the bronchial tree (airways) and total RNA (including miRNA) was extracted from the airways using the mirVana miRNA extraction kit (Ambion, USA) according to manufacturer's instructions. mRNAs were isolated from total RNA by gel electrophoresis (flashPAGE precast gels, buffer and fractionator, Ambion, USA). To quantify miRNAs amine modified NTPs were incorporated during tailing with poly(A) polymerase and the miRNAs were labelled (mirVana miRNA labelling kit, Ambion) with an amine-reactive dye (Cy3, Amersham). Dye signals were analysed following hybridization with probes (mirVana probe set, Ambion) on glass microarray slides (Australian Genome Facility, Australia) and scanned using a GenePix 4000B scanner (Axon, USA). The normalised signal intensity was expressed as a log ratio employing Genespring software (Agilent, USA).

As shown in FIG. 1, at 24 hrs the expression of 15 miRNAs was at least 1.5-fold higher in the airways of mice challenged with HDM extract when compared to those treated with saline only. All 15 upregulated miRNAs are identical in sequence between mice and humans. Two miRNAs (hsa_miR_223 and hsa_miR_21; denoted with an asterisk in FIG. 1) were more than 2-fold upregulated at 24 hrs (2.32-fold and 2.2-fold respectively). hsa_miR_145 is predicted to have 353 mRNA targets and hsa_miRNA_21 is predicted to have 157 mRNA targets.

Additional sequence information for these miRNA, including genomic location, can be found at the publically accessible miRBase database.

The sequences of the human miRNAs indicated in FIG. 1 are as follows:

```
hsa_miR_21:
5'-UAGCUUAUCAGACUGAUGUUGA-3'          (SEQ ID NO: 1)
```

-continued

```
hsa_miR_145:
5'-GUCCAGUUUUCCCAGGAAUCCCUU-3'      (SEQ ID NO: 2)

hsa_miR_133a:
5'-UUGGUCCCCUUCAACCAGCUGU-3'        (SEQ ID NO: 3)

hsa_miR_30a_5p:
5'-UGUAAACAUCCUCGACUGGAAG-3'        (SEQ ID NO: 4)

hsa_miR_29a:
5'-UAGCACCAUCUGAAAUCGGUU-3'         (SEQ ID NO: 5)

hsa_miR_22:
5'-AAGCUGCCAGUUGAAGAACUGU-3'        (SEQ ID NO: 6)

hsa_miR_27a:
5'-UUCACAGUGGCUAAGUUCCGC-3'         (SEQ ID NO: 7)

hsa_miR_23b:
5'-AUCACAUUGCCAGGGAUUACC-3'         (SEQ ID NO: 8)

hsa_miR_23a:
5'-AUCACAUUGCCAGGGAUUUCC-3'         (SEQ ID NO: 9)

hsa_let_7a:
5'-UGAGGUAGUAGGUUGUAUAGUU-3'        (SEQ ID NO: 10)

hsa_let_7b:
5'-UGAGGUAGUAGGUUGUGUGGUU-3'        (SEQ ID NO: 11)

hsa_let_7c:
5'-UGAGGUAGUAGGUUGUAUGGUU-3'        (SEQ ID NO: 12)

hsa_miR_16:
5'-UAGCAGCACGUAAAUAUUGGCG-3'        (SEQ ID NO: 13)

hsa_miR_126:
5'-UCGUACCGUGAGUAAUAAUGC-3'         (SEQ ID NO: 14)

hsa_miR_223:
5'-UGUCAGUUUGUCAAAUACCCC-3'         (SEQ ID NO: 15)
```

Additional sequence information for these miRNA, including genomic location, can be found at the publically accessible miRBase database.

Tabulation of the fold increase observed for various miRNA (showing at least a 1.5-fold increase in expression) at 24 hours post one HDM challenge are shown below in Table 2.

TABLE 2

| miRNA | fold increase |
| --- | --- |
| hsa_miR_223 | 2.316 |
| hsa_miR_21 | 2.164 |
| hsa_miR_145 | 1.887 |
| hsa_let_7c | 1.826 |
| hsa_let_7b | 1.668 |
| hsa_miR_16 | 1.627 |
| hsa_miR_126 | 1.609 |

Example 1B miRNA Expression Following HDM Allergen Challenge and Rechallenge

Airways of asthmatics are exposed to allergens on a regular basis leading to the establishment of aberrant immune responses. To model this experience, the airways of BALB/c mice were exposed to HDM allergen extract (or normal saline in controls) by intratracheal instillation as per Example 1A, and were subsequently rechallenged 10 days later. The concentrations and amounts of allergen or saline administered were the same for the initial challenge and the rechallenge. miRNAs were isolated and quantified as described in Example 1A.

As shown in Table 3 below, 24 hrs after the day 10 treatment expression levels of 9 miRNAs were found to be more than 4-fold upregulated in the airways of HDM extract challenged mice compared with those challenged with saline onlyIt will also be noted that expression of one of these miRNA species, hsa_miR_21, was also found to be upregulated by more than 2-fold following a single HDM challenge (Example 1A, FIG. 1 and Table 2). The sequence of hsa_let_7f is shown below and as SEQ ID NO:55. The remainder of the sequences for the miRNA shown in Table 3 are provided in Example 1A above.

```
hsa_let_7f:
5'-UGAGGUAGUAGAUUGUAUAGUU-3'        (SEQ ID NO: 55)
```

TABLE 3

| miRNA | fold increase |
| --- | --- |
| hsa_miR_126 | 12.76 |
| hsa_miR_21 | 9.252 |
| hsa_miR_16 | 5.932 |
| hsa_miR_29a | 4.506 |
| hsa_let_7a | 4.476 |
| hsa_miR_145 | 4.397 |
| hsa_let_7c | 4.347 |
| hsa_let_7f | 4.314 |
| ambi_miR_7029 | 4.087 |

Example 2 miRNA Expression in Ovalbumin Challenged Mice

A well established mouse model of asthma and related allergic diseases is based on sensitisation and subsequent challenge with ovalbumin (OVA). Whereas the model used in Example 1 (based on HDM extract challenge) was designed to detect miRNA involved in early stage allergic/inflammatory response in the airways, the OVA model described below provides information on established or late stage responses in whole lungs.

BALB/c mice were sensitized by intraperitoneal injection with 50 µg OVA and 1 mg Alhydrogel (aluminium hydroxide; CSL, Australia) in 0.9% sterile saline (n=4). Non-sensitized mice (n=3) received 1 mg of Alhydrogel in 0.9% sterile saline. In OVA sensitised mice, responsiveness to increasing aerosol concentrations of methacholine was determined by barometric plethysmography (in conscious unrestrained mice) and confirmed by invasive measurement of total lung resistance, dynamic compliance, and expiratory flow at 50% of tidal volume in anesthetized mice (0.2 mg/10 g xylazine and ketamine 0.4 mg/10 g), using apparatus and software supplied by Buxco (Troy, USA). The barometric plethysmography yields a dimensionless parameter known as enhanced pause (Penh) that reflects changes in waveform of the pressure signal from the plethysmography chamber combined with a timing comparison of early and late expiration. The invasive pulmonary mechanics were measured in response to methacholine in separate groups of mice. Anesthetized animals were tracheotomized and applied to the Buxco restrained animal chamber. Ventilation rate was set at 130 strokes/minute and 175 µL stroke volume. The effective range of peak end expiratory pressure was set between ±25 cm $H_2O$, the flow transducer was calibrated to 1 ml air injected by a syringe. Animals were given time to acclimate and then exposed to increasing vaporized concentrations of methacholine. Differences in pressure and flow parameters were collected by Buxco's software (Biosystem XA for windows) and analysed according to Buxco's recommended internal algorithm. The above described measurements were used to confirm bronchial hyperresponsiveness in OVA sensitised mice, thereby confirming the validity of these mice as a model of asthma and related diseases.

On day 7 ovalbumin-sensitized mice received 50 µl ovalbumin (1 mg/ml in 0.9% sterile saline) intra-nasally following light isoflurane anesthesia, and non-sensitized received sterile 0.9% saline intra-nasally after light isoflurane anesthesia. This procedure was followed for 6 days. Mice were sacrificed on day 13, 24 hrs after the final intra-nasal administration.

Whole lungs were removed and total RNA and miRNA extracted as described in Example 1. miRNA expression patterns were also determined as described in Example 1.

Figure 3:
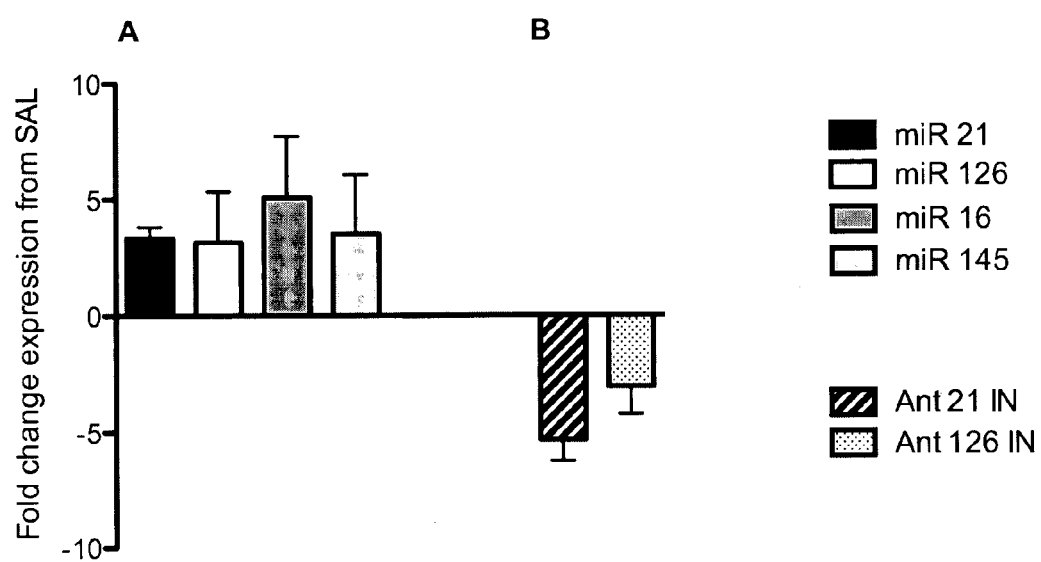
FIG. 3. Validation of miRNA array data by qRT-PCR and inhibition of miRNAs by antagomirs in-vivo. A. miR-21, -126, -16, -145 were quantified by quantitative real-time polymerase chain reaction (qRT-PCR) in mice (n=3) 24 hr after a second challenge (day 0 and day 10) with 50 μg house dust mite extract (HDM) when compared to saline challenged mice (SAL, baseline, n=3). B. HDM-challenged mice (n=3 per group) were treated with an antisense oligonucleotide (antagomir) directed against miR-126 (Ant 126) or miR-21 (Ant 21) intranasally (IN) 24 hrs prior to second HDM challenge. miR-126 and miR-21 were quantified by qRT-PCR and compared to normal saline challenged mice (SAL, baseline).

18 miRNAs were differentially expressed between allergic and non-allergic mice in the lung (p<0.05). hsa_miR_24, hsa_miR_23a, hsa_miR_30c, hsa_miR_25, hsa_miR_15b, hsa_miR_181b, hsa_miR_150, hsa_miR_361, hsa_miR_345, and ambi_miR_7031 were down-regulated in OVA sensitised/challenged mice, whilst mmu_miR_294, hsa_miR_136, ambi_miR_7065, ambi_miR_7099, hsa_miR_181a, mmu_miR_325, ambi_miR_7021 and ambi_miR_7008 were upregulated. It will be noted that one of the downregulated miRNAs as indicated in FIG. 3, hsa_miR_23a (SEQ ID NO:9), was found to be upregulated following exposure to HDM extract (see Example 1A). Without wishing to be bound by theory, this may suggest that the miRNAs involved in the early stages of an inflammatory response differ from those involved in the later stages and/or that the role(s) played by individual miRNAs may alter through the course of an inflammatory response, possibly resulting from regulation of multiple targets. That is, the spatial and/or temporal expression pattern of individual miRNAs may vary in early and late stage inflammatory responses.

The sequences of the remaining human (hsa) and mouse (mmu) miRNAs indicated in FIG. 3 are as follows:

```
hsa_miR_24:
5'-GUGCCUACUGAGCUGAUAUCAGU-3'      (SEQ ID NO: 16)

hsa_miR_30c:
5'-UGUAAACAUCCUACACUCUCAGC-3'      (SEQ ID NO: 17)

hsa_miR_25:
5'-CAUUGCACUUGUCUCGGUCUGA-3'       (SEQ ID NO: 18)

hsa_miR_15b:
5'-UAGCAGCACAUCAUGGUUUACA-3'       (SEQ ID NO: 19)

hsa_miR_181b:
5'-AACAUUCAUUGCUGUCGGUGGG-3'       (SEQ ID NO: 20)

hsa_miR_150:
5'-UCUCCCAACCCUUGUACCAGUG-3'       (SEQ ID NO: 21)

hsa_miR_361:
5'-UUAUCAGAAUCUCCAGGGGUAC-3'       (SEQ ID NO: 22)

hsa_miR_345:
5'-UGCUGACUCCUAGUCCAGGGC-3'        (SEQ ID NO: 23)

hsa_miR_136:
5'-ACUCCAUUUGUUUUGAUGAUGGA-3'      (SEQ ID NO: 24)

hsa_miR_181a:
5'-AACAUUCAACGCUGUCGGUGAGU-3'      (SEQ ID NO: 25)

mmu_miR_294:
5'-AAAGUGCUUCCCUUUUGUGUGU-3'       (SEQ ID NO: 26)

mmu_miR_325:
5'-CCUAGUAGGUGCUCAGUAAGUGU-3'      (SEQ ID NO: 27)
```

Additional sequence information for these miRNA, including genomic location, can be found at the publically accessible miRBase database.

Example 3

Antisense-mediated Suppression of miRNA Expression

Figure 4:
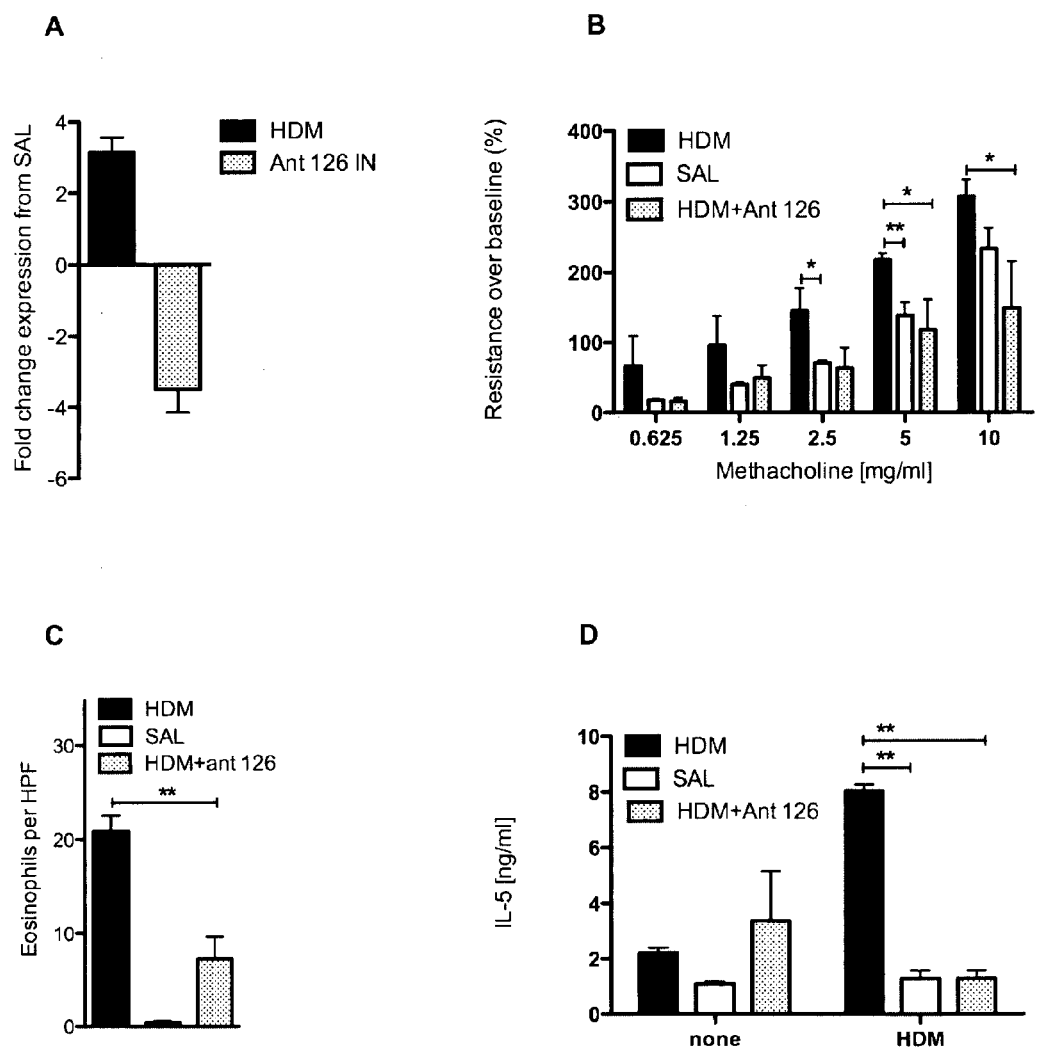
FIG. 4. Treatment with antisense oligonucleotide Ant 126 inhibited miR-126 expression in the airway wall (A), the development of airway hyperreactivity (B), eosinophilic airway inflammation (C) and interleukin-5 (IL-5) release in-vivo (D) in HDM allergic mice (n=4-6 mice per group). (*p<0.05, **p<0.01).

Quantitative RT-PCR was used to validate the expression data obtained by microarray analysis (se above) for four miRNAs, hsa_miR_21, hsa_miR_126, hsa_miR_16 and hsa_miR_145. qRT-PCR was performed using the TaqMan® Gene Expression Assays (Applied Biosystems) with primers supplied by the manufacturers. miRNA expression was normalised to 18S RNA. miRNA was extracted from mice (n=3) as described in Example 1A 24 hr after a second challenge (day 0 and day 10) with 50 µg house dust mite extract (HDM) (as per Example 1B). As shown in FIG. 4A, expression of all four miRNAs from HDM challenged mice was significantly increased when compared to saline challenged mice (SAL, baseline, n=3).

To determine the ability of antisense constructs to successfully inhibit expression of miRNAs, HDM-challenged mice were treated with an antisense oligonucleotides against hsa_miR_126 (Ant 126) and hsa_miR_21 (Ant 21), (see Example 4 below) and expression of these miRNAs was subsequently determined by qRT-PCR as described above. The sequences of Ant 126 and Ant 21 are shown below and in SEQ ID Nos: 56 and 57 respectively.

```
Ant 126:
                                   (SEQ ID NO: 56)
5'-mG.*.mC.*.mA.mU.mU.mA.mU.mU.mA.mC.mU.mC.mA.mC.
mG.mG.mU.mA.*.mC.*.mG.*.mA.*.-3'-Chl

Ant 21:
                                   (SEQ ID NO: 57)
5'-mU.*.mC.*.mA.mA.mC.mA.mU.mC.mA.mG.mU.mC.mU.mG.
mA.mU.mA.mA.mG.*.mC.*.mU.*.mA.*-3'-Chl
```

(where m=2'-OMe modified phosphoramidite, *=phosphorothioate linkage, and -Chl=hydroxyprolinol linked cholesterol).

As shown in FIG. 3B, the expression of both hsa_miR_126 and hsa_miR_21 was significantly reduced following administration to the mice 24 hours earlier of the corresponding antisense oligonucleotides when compared with saline challenged mice (SAL, baseline).

Example 4

Antisense-mediated Suppression of Allergic Airways Disease Symptoms in HDM Challenged Mice An antisense oligonucleotide against hsa_miR_126 was designed and produced, designated Ant 126. Ant 126 was used in the HDM allergen mouse model (see Example 1) to determine the ability of an miRNA-specific antisense oligonucleotide to inhibit or suppress features characteristic of allergic airways disease. The sequence of Ant 126 is shown below:

(SEQ ID NO: 56)
5'-mG.*.mC.*.mA.mU.mU.mA.mU.mU.mA.mC.mU.mC.mA,mC.
mG.mG,mU.mA.*.mC.*.mG.*.mA.*.-3'-Chl (where m=2'-OMe modified phosphoramidite, *=phosphorothioate linkage, and -Chl=hydroxyprolinol linked cholesterol).

BALB/c mice were given 50 μg house dust mite extract (HDM) dissolved in 50 μl or 50 μl normal saline (SAL) intranasally under light isoflurane anaesthesia at day 0, day 1, and, day 2. At day 13, day 14, day 15, and day 16 all mice were challenged with 5 μg house dust mite extract (HDM, allergic mice) or normal saline (SAL, control mice). Some mice also received Ant 126 dissolved in 50 μl of nuclease free water or 50 μl nuclease free water only (control) at day 12, day 14, and day 16 intranasally (3.75 nmol/application). Mice were tested for airway hyperreactivity at day 17 and then sacrificed to collect tissue samples. In the analyses described below the significance of differences between groups was analyzed using Student's t-test or Mann-Witney test as appropriate.

Airway hyperreactivity (AHR) was assessed invasively by measurement of total lung resistance in response to increasing aerosol concentrations of methacholine (0.625 mg/ml to 10 mg/ml) in anesthetized mice (0.2 mg/10 g xylazine and ketamine 0.4 mg/10 g), using apparatus and software supplied by Buxco (USA). Anesthetized animals were tracheotomized and applied to the Buxco restrained animal chamber. Ventilation rate was set at 150 strokes per minute and 175 μl stroke volume. The effective range of peak end expiratory pressure was set between ±25 cm $H_2O$, the flow transducer was calibrated to 1 ml air injected by a syringe. Animals were given time to acclimate and then exposed to increasing vaporized concentrations of methacholine. Differences in pressure parameters were collected by Buxco's software (Biosystem XA for windows) and analysed according to Buxco's recommended internal algorithm. Percentage increase over baseline (water) of resistance was calculated for each dose. As shown in FIG. 4B, significant reduction in lung resistance ($*p<0.05$, $**p<0.01$) was observed in HDM-challenged mice administered Ant 126 when compared to HDM-challenged mice in the absence of Ant 126 administration.

To assess cellular inflammation, lung tissue was stained, eosinophils identified by morphological criteria, and quantified by counting ten high power fields. As shown in FIG. 4C, a significant reduction in eosinophil numbers ($p<0.01$) was observed in HDM-challenged mice administered Ant 126 when compared to HDM-challenged mice in the absence of Ant 126 administration. To determine concentrations of the cytokine IL-5, peribronchial lymph node cells were excised, filtered, and cultured ($5 \times 10^6$ per ml) in the presence or absence of 50 μg/ml house dust mite (optimal concentration) for 6 days. IL-5 concentrations were then measured in supernatants by ELISA (BD Biosciences Pharmingen). As shown in FIG. 4D, a significant reduction was observed in IL-5 concentration ($p<0.01$) in HDM-challenged mice administered Ant 126 when compared to HDM-challenged mice in the absence of Ant 126 administration.

These data demonstrate the efficacy of antisense oligonucleotides directed against upregulated miRNA in the suppression of hallmarks of allergic airways diseases such as asthma in a validated mouse model.

The invention claimed is:

1. A method for treating or preventing an inflammatory condition of the airways in a subject, the method comprising administering to the subject an effective amount of an antagonist of hsa_miR_126, wherein the antagonist is an antisense oligonucleotide that recognizes said hsa_miR_126 and the inflammatory condition of the airways is asthma.

2. The method of claim 1 wherein said hsa_miR_126 comprises the nucleotide sequence as set forth in SEQ ID No: 14.

3. The method of claim 1 wherein the antisense oligonucleotide comprises the nucleotide sequence as set forth in any one of SEQ ID Nos: 41 or 56.

4. The method of claim 1 wherein the antisense oligonucleotide sequence comprises one or more modifications.

5. The method of claim 1 wherein the miRNA is hsa_miR_126 and the antagonist comprises the sequence:

(SEQ ID NO: 56)
5'- mG.*.mC.*.mA.mU.mU.mA.mU.mU.mA.mC.mU.mC.mA.mC.

mG.mG.mU.mA.*.mC.*.mG.*.mA.*.-3'-Chl, where m=2'-OMe modified phosphoramidite, *=a phosphorothioate linkage, and -Chl =hydroxyprolinol linked cholesterol.

* * * * *